United States Patent
Charlier et al.

(10) Patent No.: US 7,834,759 B2
(45) Date of Patent: Nov. 16, 2010

(54) WIRELESS SENSOR AND SYSTEM THAT DETERMINES EXPOSURE TO AN ENVIROMENTAL ELEMENT BASED ON LOCAL CONDITIONS

(75) Inventors: Michael Charlier, Palatine, IL (US); Jin Kim, Pleasant Prairie, WI (US); Michael Masquelier, Barrington, IL (US)

(73) Assignee: Motorola, Inc., Schaumburg, IL (US)

( * ) Notice: Subject to any disclaimer, the term of this patent is extended or adjusted under 35 U.S.C. 154(b) by 448 days.

(21) Appl. No.: 11/946,585

(22) Filed: Nov. 28, 2007

(65) Prior Publication Data

US 2009/0135003 A1    May 28, 2009

(51) Int. Cl.
*G08B 1/08* (2006.01)
(52) U.S. Cl. .................. 340/539.12; 340/600; 600/407; 250/372
(58) Field of Classification Search ............ 340/539.11, 340/539.12, 539.16, 539.26, 539.28, 539.29, 340/600; 600/407; 250/372
See application file for complete search history.

(56) References Cited

U.S. PATENT DOCUMENTS

| 5,036,311 | A | 7/1991 | Moran et al. |
| 5,365,068 | A | 11/1994 | Dickerson |
| 5,382,986 | A | 1/1995 | Black et al. |
| 5,995,862 | A * | 11/1999 | Gallorini .................... 600/407 |
| 7,073,129 | B1 | 7/2006 | Robarts et al. |
| 2004/0031927 | A1 | 2/2004 | Tsai et al. |
| 2004/0149921 | A1 | 8/2004 | Smyk |
| 2005/0264752 | A1 | 12/2005 | Howell et al. |
| 2006/0001827 | A1 | 1/2006 | Howell et al. |
| 2006/0151709 | A1 | 7/2006 | Hahl |
| 2006/0250261 | A1 | 11/2006 | Henrie et al. |

FOREIGN PATENT DOCUMENTS

| EP | 1653204 A1 | 5/2006 |
| WO | 2004072594 A1 | 8/2004 |

OTHER PUBLICATIONS http://www2.oregonscientific.com/shop/product.asp?cid=2&scid=5&pid=644.
http:/www.partshelf.com/ci00913.html.
http:/www.wirelessalarm.com/NU300.html.
http://www.professionalequipment.com/chemical-detection-device-chameleon-starter-kit-085100/multi-gas-meters.
http://apps.em.doe.gov/OST/pubs/itsrs/itsr2104.pdf; "Wireless Remote Radiation Monitoring System".

* cited by examiner

*Primary Examiner*—Jeffery Hofsass
(74) *Attorney, Agent, or Firm*—Matthew C. Loppnow; Prass LLP

(57) ABSTRACT

A system (100) that determines exposure based on local conditions is disclosed. The system can include a sensor (172) configured to sense local conditions local to a user of the system, a sensor local wireless transmitter (174) coupled to the sensor, and an electronic device (105). The electronic device can include a controller (120) configured to control operations of the electronic device, a device local wireless transceiver (155) coupled to the controller and wirelessly coupled to the sensor local wireless transmitter, a network interface coupled (150) to a wide area network and coupled to the controller, the network interface configured to obtain local environmental conditions, and an exposure module (190) coupled to the controller. The exposure module can determine exposure to an environmental element based at least on the local conditions sensed by the sensor and the local environmental conditions obtained by the network interface.

20 Claims, 4 Drawing Sheets

WIRELESS SENSOR AND SYSTEM THAT DETERMINES EXPOSURE TO AN ENVIROMENTAL ELEMENT BASED ON LOCAL CONDITIONS

BACKGROUND

1. Field

The present disclosure is directed to a wireless sensor and system that determines exposure based on local conditions. More particularly, the present disclosure is directed to a system that determines exposure to an environmental element based at least on local conditions sensed by the sensor and local environmental conditions obtained by a network interface.

2. Introduction

Presently, exposure to environmental hazards such as ultraviolet radiation, air pollution, or allergens, such as pollen, ragweed, mold, etc. can lead to immediate health problems like sun-burn, and asthma or even longer term health consequences, such as skin or lung cancer. People are often not aware of the danger until it is too late. For example, if a person has been out in the sun all afternoon and is near the recommended ultraviolet exposure level, but the time is 6:00 PM, there is no need to apply additional sun tan lotion. However, if the same person had been outside all morning and the time is 1:00 PM with a sunny forecast, then the user may be at risk of overexposure to ultraviolet rays from the sun. As another example, a person may be working in a factory where low levels of exposure to materials, such as biological agents or radiation, can be acceptable over a short period of time. However, there may be a leak of the materials, which can decrease the allowable exposure time or the person may have left the area for frequent breaks, which can increase the allowable exposure time.

There are current systems that perform ultraviolet exposure evaluations. However, these systems have problems because they do not take into account variable local conditions. These variable local conditions can include partially cloudy days in a region or proximity to water where reflections can amplify the cumulative exposure.

Unfortunately, people who enjoy outdoor activities do not have an accurate way to determine the risk of being exposed to a high cumulative level of ultraviolet radiation that could lead to sunburn or long term skin damage. Additionally, these people cannot rely on current systems because current systems do not take variable factors into account, such as variations in ultraviolet levels based on location. For example these variations can be based on movement through shaded and un-shaded areas.

Therefore, a need exists for a health management system that takes into account both the accumulated exposure and a prediction of future exposure limits before a potentially dangerous level of exposure is reached.

SUMMARY

A system that takes into account accumulated exposure and forecast environmental conditions; and provides a prediction of future exposure limits before a potentially dangerous level of exposure is reached. The system can include a sensor configured to sense local conditions local to a user of the system, a sensor local wireless transmitter coupled to the sensor, and an electronic device. The electronic device can include a controller configured to control operations of the electronic device, a device local wireless transceiver coupled to the controller and wirelessly coupled to the sensor local wireless transmitter, a network interface coupled to a wide area network and coupled to the controller, the network interface configured to obtain local environmental conditions, and an exposure module coupled to the controller. The exposure module can determine exposure to an environmental element based at least on the local conditions sensed by the sensor and the local environmental conditions obtained by the network interface.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION

Figure 1:
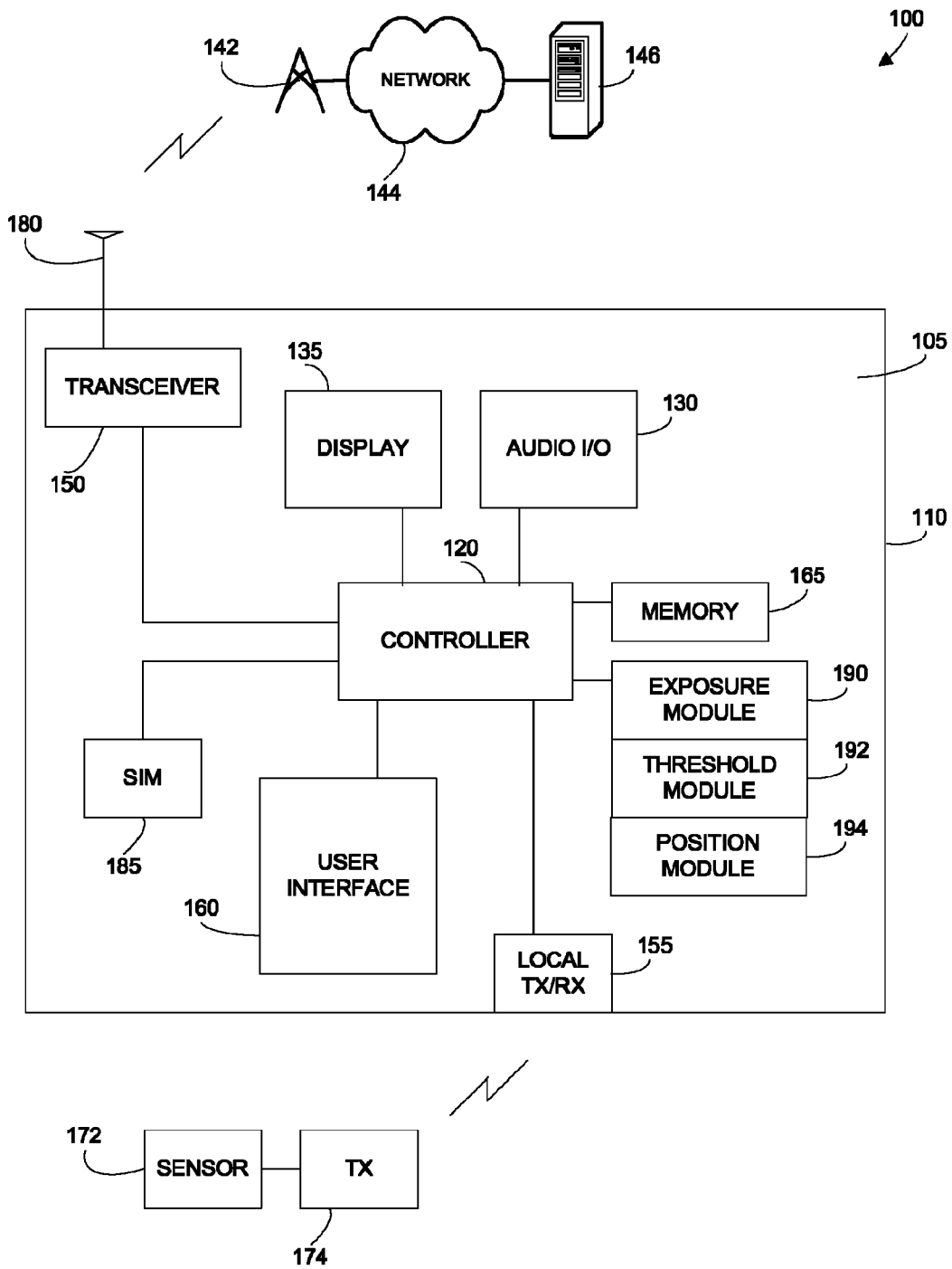
FIG. 1 is an exemplary block diagram of a system according to one embodiment.

FIG. 1 is an exemplary block diagram of a system 100 according to one embodiment. The system 100 can include a sensor 172 and a sensor local wireless transmitter 174 coupled to the sensor 172. The sensor 172 can sense local conditions local to a user of the system. For example, the sensor 172 can be a weather sensor, such as an ultraviolet sensor for sensing ultraviolet exposure, a biological sensor for sensing gases, radiation, or the like, a biometric sensor for sensing a user's heart rate, blood pressure, or the like, or any other sensor for sensing local conditions. The local conditions can include weather conditions, such as ultraviolet conditions or biological exposure conditions, personal conditions, such as a heart rate of a user, or other local conditions. The sensor 172 may be located anywhere it can be useful to a user. For example, the sensor 172 may be located on sunglasses, on an identification badge, on a surfboard, on a helmet, on a ski, on an arm band, on a bicycle, on handlebars, or anywhere else it can be used to sense local conditions affecting a user. The local wireless transmitter 174 can include an antenna and can transmit using a local wireless communications protocol, such as Bluetooth, WiFi, 802.15.4, 802.11, Zigbee, Near Field Communication (NFC), Radio Frequency Identification (RFID), or any other short range wireless connectivity.

The system 100 can also include an electronic device 105. The electronic device 105 may be a wireless communication device, such as a wireless telephone, a cellular telephone, a personal digital assistant, a pager, a personal computer, a selective call receiver, or any other device that is capable of sending and receiving communication signals on a network including wireless network. The electronic device 105 can include a housing 110, a controller 120 coupled to the housing 110, audio input and output circuitry 130 coupled to the housing 110, a display 135 coupled to the housing 110, a transceiver 150 coupled to the housing 110, a user interface 160 coupled to the housing 110, a memory 165 coupled to the housing 110, a device local wireless transceiver 155 coupled to the controller and wirelessly coupled to the sensor local wireless transmitter 174 and an antenna 180 coupled to the housing 110 and the transceiver 150. The electronic device 105 can also include an exposure module 190, a threshold module 192, and a position determination module 194. The exposure module 190, the threshold module 192, and/or the position determination module 194 can be coupled to the controller 120, can reside within the controller 120, can reside within the memory 165, can be autonomous modules, can be software, can be hardware, or can be in any other format useful for a module on a electronic device 105. The exposure module 190 and/or the threshold module 192 may be located at the sensor 172, on the device 105, and/or at the server 146.

The display 135 can be a liquid crystal display (LCD), a light emitting diode (LED) display, a plasma display, or any other means for displaying information. The transceiver 150 may include a transmitter and/or a receiver. The audio input and output circuitry 130 can include a microphone, a speaker, a transducer, or any other audio input and output circuitry. The user interface 160 can include a keypad, buttons, a touch pad, a joystick, an additional display, or any other device useful for providing an interface between a user and an electronic device. The memory 165 may include a random access memory, a read only memory, an optical memory, a subscriber identity module memory, or any other memory that can be coupled to a wireless communication device. The device local wireless transceiver 155 may include an antenna.

The transceiver 150 can provide a network interface to a wireless wide area network, such as a network 144 via a base station or access point 142. The network 144 may include any type of network that is capable of sending and receiving signals, such as wireless signals. For example, the network 144 may include a wireless telecommunications network, a cellular telephone network, a Time Division Multiple Access (TDMA) network, a Code Division Multiple Access (CDMA) network, a wireless local area network, a satellite communications network, and other like communications systems. Furthermore, the network 144 may include more than one network and may include a plurality of different types of networks. Thus, the network 144 may include a plurality of data networks, a plurality of telecommunications networks, a combination of data and telecommunications networks and other like communication systems capable of sending and receiving communication signals. A server 146 can be coupled to the network 144.

In operation, the controller 120 can control operations of the electronic device 105. The network interface 150 can obtain local environmental conditions from the server 146. The exposure module 190 can determine exposure to an environmental element based at least on the local conditions sensed by the sensor 172 and the local environmental conditions obtained by the network interface 150. The exposure module 190 can determine exposure locally or by contacting the remote server 146 for assistance in the determination.

The exposure module 190 can determine exposure to an environmental element based at least on local ultraviolet conditions, local weather conditions, a time of day, and/or information about the user. The information about the user can be a skin type of the user and/or a sun protection factor of sun protection worn by the user. Sun protection may include sunscreen lotion, clothing worn by a user, or other elements that can affect a sun protection factor.

A speaker in the audio input and output circuitry 130 can provide an audible alert to warn the user of overexposure to an environmental element based on the sensed local conditions.

The memory 165 can store information regarding cumulative environmental element exposure based on the sensed local conditions. Such a memory may be located at the sensor 172, at the device 105, and/or at the server 146. The threshold module 192 can enable the exposure module 190 after detecting a threshold of environmental element exposure has been reached based on the sensed local conditions. The threshold module 192 may also be located at the sensor 172, at the device 105, and/or at the server 146.

The exposure module 190 can determine the exposure by predicting future exposure based at least on the local conditions sensed by the sensor 172 and/or the local environmental conditions obtained by the network interface 150. The display 135 can display a level of current exposure to the environmental element and/or display a predicted future level of exposure to the environmental element. The position determination module 194 can determine a current location or local position of the device 105. The local conditions can include forecast data based on the current location of the device 105 determined by the position determination module 194. The network interface 150 can obtain local environmental conditions by sending the local position of the device 105 to the server 146 and by receiving local environmental conditions based on the local position of the device 105. The exposure module 190 may also predict overexposure based at least on the local conditions sensed by the sensor 172 and the local environmental conditions obtained by the network interface 150. The display 135 can then provide, based on the predicted overexposure and based on the position of the device 105, information about an alternate location to reduce overexposure. For example, the display 135 may inform the user to obtain shade in a local hotel or restaurant if the user risks overexposure to ultraviolet rays from the sun.

Thus, the present disclosure can provide a system 100 to acquire data from a sensor 172 that can be placed in a spot likely to receive the highest level of exposure. For example, an ultraviolet sensor can be located on sunglasses by the nose and/or ears of a user. The system 100 can combine the sensor data with information available from an electronic device 105, such as a cellular phone. This information can include the device location, time, personal profile data, sun protection data input by the user, and other useful information. The data can also be combined with server based forecasts, such as weather forecasts, to predict exposure danger, such as ultraviolet light exposure danger, if the individual continues to remain in their current location. The predicted exposure information can be based on time versus the amount of exposure.

According to a related embodiment, the system 100 can include an ultraviolet sensor 172 that can be worn by a user and that can sense local ultraviolet conditions. The ultraviolet sensor 172 can be coupled to a sensor local wireless transmitter 174. The system 100 can also include an electronic device 105. The electronic device 105 can include a controller 120, a device local wireless transceiver 155 coupled to the controller and wirelessly coupled to the sensor local wireless transmitter 174, a position determination module 194 configured to determine a local position of the electronic device 105, and a network interface 150, such as a cellular transceiver, coupled to a wide area network 144 and coupled to the controller 120. The network interface 150 can obtain local weather conditions by sending the local position of the electronic device 105 to a server 146 and by receiving the local weather conditions based on the local position of the electronic device 105. The electronic device 105 can also include an ultraviolet exposure module 190 that can determine ultraviolet exposure based at least on the local ultraviolet conditions sensed by the ultraviolet sensor 172 and the local weather conditions obtained by the network interface 150.

The electronic device 105 can also include a threshold module 192 that can enable the ultraviolet exposure 190 module after detecting a threshold of ultraviolet light sensed by the ultraviolet sensor 172 has been reached. The electronic device 105 can also include a display 135 that can display a level of current exposure to ultraviolet light and display a predicted future level of exposure to ultraviolet light. The ultraviolet sensor 172 and the sensor local wireless transmitter 174 can be coupled to a frame of eyewear that can be worn by the user. The eyewear can also include an audio interface coupled to the frame and coupled to the sensor local wireless transmitter 174. The audio interface can include a microphone and a speaker.

Figure 2:
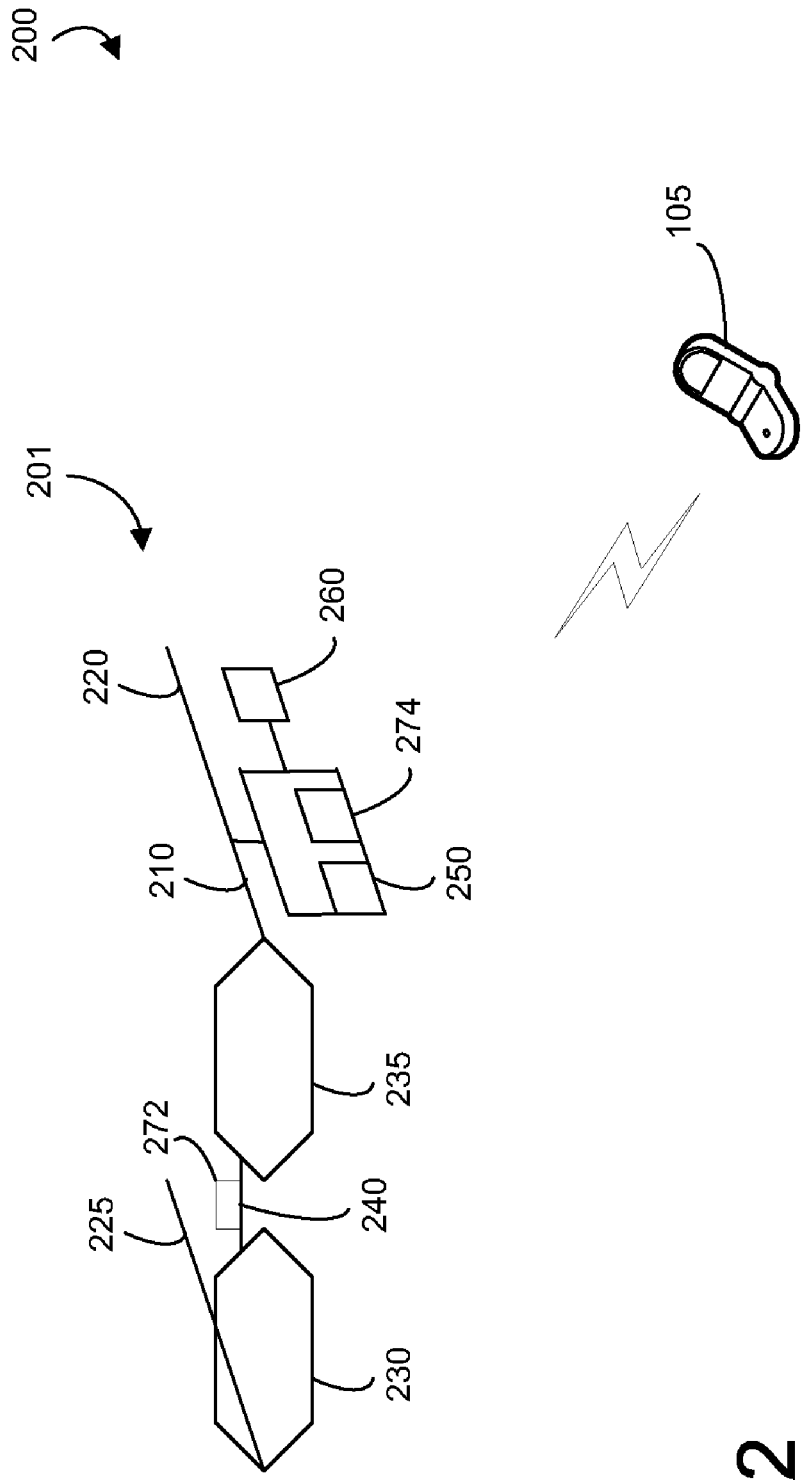
FIG. 2 is an exemplary illustration of a system according to a related embodiment.

FIG. 2 is an exemplary illustration of the system 200 according to a related embodiment. The system 200 can include the electronic device 105 and eyewear 201. The eyewear 201 can be sunglasses worn by a user to reduce light reaching the user's eyes. The eyewear 201 can include a frame 210, an ultraviolet sensor 272 coupled to the frame, and a sensor local wireless transmitter 274 coupled to the ultraviolet sensor 272. The eyewear 201 can also include lenses 230 and 235 coupled to the frame 210, a bridge 240 coupling the lenses 230 and 235 to each other, and temples 220 and 225 for placing the eyewear 201 on the ears of a user. The eyewear 201 can further include a microphone 250 and a speaker 260 coupled to the sensor local wireless transmitter 274. The ultraviolet sensor 272 can be placed on the bridge 272, on the temple 220 close to a user's ear, or any other ideal location for detecting actual exposure in the most susceptible places.

In operation, the ultraviolet sensor 272 can sense local ultraviolet conditions. A position determination module in the device 105 can determine a local position of the device 105. A wireless wide area network transceiver in the device 105 can be wirelessly coupled to a wireless wide area network and can obtain local weather conditions by sending the local position of the device 105 to a server and by receiving local weather conditions based on the local position of the device 105. An ultraviolet exposure module in the device 105 can determine ultraviolet exposure based at least on the local weather conditions sensed by the ultraviolet sensor 272 and based on the local weather conditions obtained by the network interface. The microphone 250 and the speaker 260 can allow a user to communicate with other devices via the device 105 using short range wireless communications with the device 105. Other elements may be included in the eyewear 201. For example, the eyewear 201 may include a light emitting diode (LED) or a heads-up display to provide visual exposure information to a user. Haptics may also be used to provide kinesthetic feedback to the user, such as an alert about overexposure. Furthermore, the speaker 260 may also provide audible feedback, warnings, and information about exposure.

Figure 3:
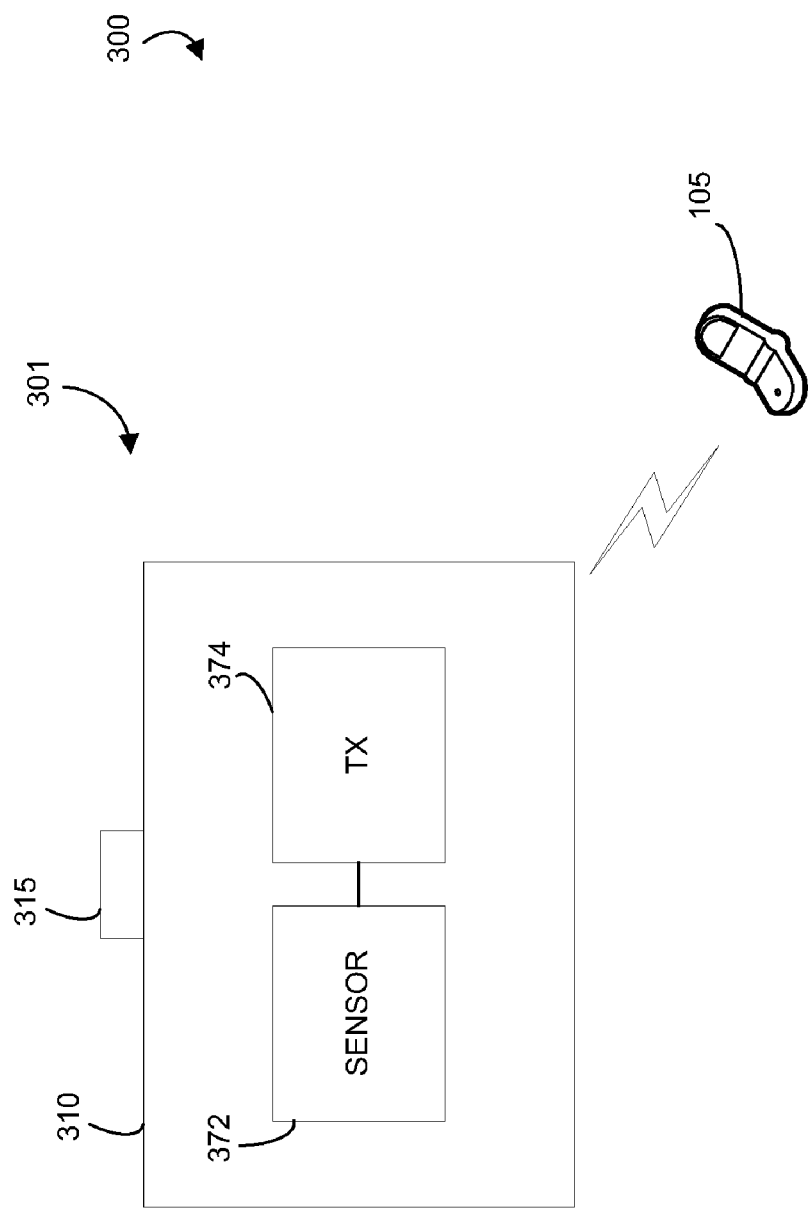
FIG. 3 is an exemplary illustration of a system according to another related embodiment.

FIG. 3 is an exemplary illustration of a system 300 according to a related embodiment. The system 300 can include the electronic device 105 and an identification badge 301. The identification badge 301 can include a frame 310, an attachment section 315, a sensor 372, and a transmitter 374. The attachment section 315 may be a clip, a lanyard, a pin, or any other attachment method for attaching a badge to an article worn or used by a user. The sensor 372 in the identification badge 301 can be used to sense environmental conditions in a workplace or other area where an employee uses such a badge and is potentially exposed to environmental materials that may affect the employee. For example, the sensor 372 can detect gasses, radiation, biological agents, asbestos, or other environmental materials that may affect an employee.

Figure 4:
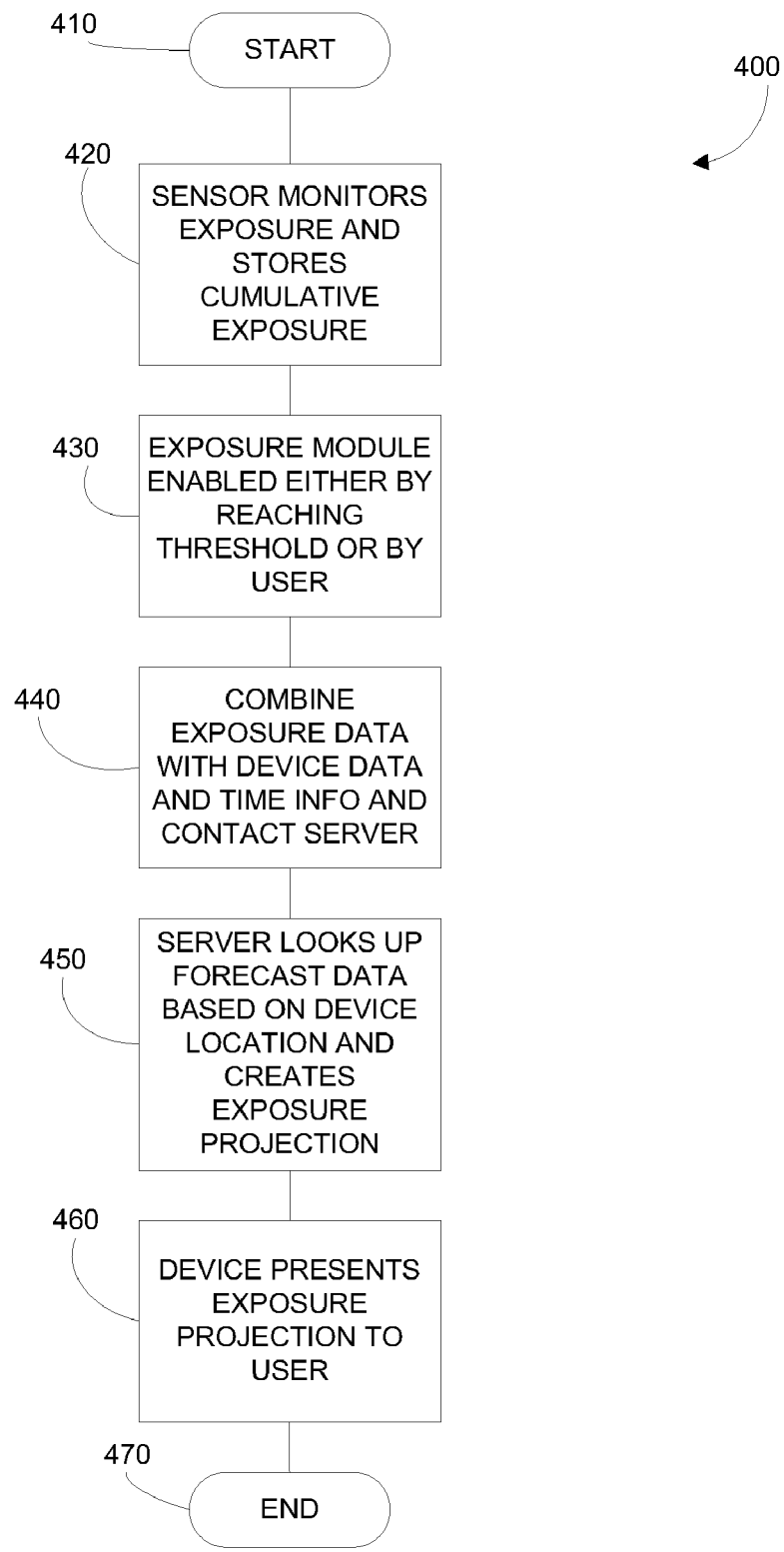
FIG. 4 is an exemplary flowchart outlining the operation of a system according to a related embodiment.

FIG. 4 is an exemplary flowchart 400 outlining the operation of the system 100 according to a related embodiment. In step 410, the flowchart begins. In step 420, the sensor 172 can monitor exposure and store the cumulative exposure. For example, the sensor 172 can monitor an ultraviolet level over time and store the cumulative ultraviolet exposure. Cumulative exposure data can be stored local to the sensor 172, in the device 105, or in the server 146. In step 430, the exposure module 190 can be enabled by the threshold module 192 detecting an exposure threshold has been reached or enabled by a user enabling the exposure module 190. In step 440, the exposure data can be combined with device data and time information and the server 146 can be contacted for additional information. In step 450, the server 146 can access the additional information, such as information relevant to future potential exposure, such as past, present, and future exposure conditions and create a future exposure projection. Alternately, the additional information can be provided to the device 105 and the device 105 can generate the future exposure projection. Furthermore, historical device and/or user position patterns can be used as part of the additional information as a predictor for exposure. In step 460, the device 105 can present an exposure projection to the user and can also make recommendations for user activity to reduce exposure. In step 470, the flowchart 400 ends.

The method of this disclosure is preferably implemented on a programmed processor. However, the controllers and modules may also be implemented on a general purpose or special purpose computer, a programmed microprocessor or microcontroller and peripheral integrated circuit elements, an integrated circuit, a hardware electronic or logic circuit such as a discrete element circuit, a programmable logic device, or the like. In general, any device on which resides a finite state machine capable of implementing the disclosed methods may be used to implement the processor functions of this disclosure.

While this disclosure has been described with specific embodiments thereof, it is evident that many alternatives, modifications, and variations will be apparent to those skilled in the art. For example, various components of the embodiments may be interchanged, added, or substituted in the other embodiments. Also, all of the elements of each figure are not necessary for operation of the disclosed embodiments. For example, one of ordinary skill in the art of the disclosed embodiments would be enabled to make and use the teachings of the disclosure by simply employing the elements of the independent claims. Accordingly, the preferred embodiments of the disclosure as set forth herein are intended to be illustrative, not limiting. Various changes may be made without departing from the spirit and scope of the disclosure.

In this document, relational terms such as "first," "second," and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a," "an," or the like does not, without more constraints, preclude the existence of additional identical elements in the process, method, article, or apparatus that comprises the element. Also, the term "another" is defined as at least a second or more. The terms "including," "having," and the like, as used herein, are defined as "comprising."

We claim:

1. A system comprising:
   a sensor configured to sense local conditions local to a user of the system;
   a sensor local wireless transmitter coupled to the sensor; and
   an electronic device, the electronic device including:
      a controller configured to control operations of the electronic device;
      a device local wireless transceiver coupled to the controller and wirelessly coupled to the sensor local wireless transmitter;
      a network interface coupled to a wide area network and coupled to the controller, the network interface configured to obtain local environmental conditions; and
      an exposure module coupled to the controller, the exposure module configured to determine exposure to an environmental element based at least on the local conditions sensed by the sensor and the local environmental conditions obtained by the network interface,
   wherein the system further comprises a position determination module configured to determine a local position of the electronic device, and
   wherein the network interface is configured to obtain local environmental conditions by sending the local position of the electronic device to a server and by receiving local environmental conditions based on the local position of the electronic device.

2. The system according to claim 1, wherein the network interface comprises a cellular transceiver.

3. The system according to claim 1, wherein the exposure module is configured to determine exposure to an environmental element based at least on local ultraviolet conditions, local weather conditions, a time of day, and information about the user.

4. The system according to claim 3, wherein information about the user comprises at least a skin type of the user and a sun protection factor of sun protection worn by the user.

5. The system according to claim 1, wherein the electronic device further comprises a speaker coupled to the controller, wherein the speaker provides an audible alert to warn the user of overexposure to an environmental element based on the sensed local conditions.

6. The system according to claim 1, further comprising a memory configured to store information regarding cumulative environmental element exposure based on the sensed local conditions.

7. The system according to claim 1, further comprising a threshold module configured to enable the exposure module after detecting a threshold of environmental element exposure has been reached based on the sensed local conditions.

8. The system according to claim 1, wherein the exposure module is configured to determine the exposure by predicting future exposure based at least on the local conditions sensed by the sensor and the local environmental conditions obtained by the network interface.

9. The system according to claim 1, further comprising a display configured to display a level of current exposure to the environmental element and display a predicted future level of exposure to the environmental element.

10. The system according to claim 1, wherein the electronic device includes a position determination module coupled to the controller and wherein the local environmental conditions include forecast data based on a current location of the electronic device determined by the position determination module.

11. The system according to claim 1,
   wherein the exposure module is configured to predict overexposure based at least on the local conditions sensed by the sensor and the local environmental conditions obtained by the network interface, and
   wherein the electronic device further comprises a display coupled to the controller, wherein the display provides, based on the predicted overexposure and based on the position of the electronic device, information about an alternate location to reduce overexposure.

12. The system according to claim 1, wherein the sensor comprises an ultraviolet sensor and the environmental conditions comprise weather conditions.

13. A system comprising:
   an ultraviolet sensor configured to be worn by a user, the ultraviolet sensor configured to sense local ultraviolet conditions;
   a sensor local wireless transmitter coupled to the ultraviolet sensor; and
   an electronic device, the electronic device including:
      a controller;
      a device local wireless transceiver coupled to the controller and wirelessly coupled to the sensor local wireless transmitter;
      a position determination module configured to determine a local position of the electronic device;
      a network interface coupled to a wide area network and coupled to the controller, the network interface configured to obtain local weather conditions by sending the local position of the electronic device to a server and by receiving local weather conditions based on the local position of the electronic device; and
      an ultraviolet exposure module configured to determine ultraviolet exposure based at least on the local ultraviolet conditions sensed by the ultraviolet sensor and the local weather conditions obtained by the network interface.

14. The system according to claim 13, further comprising a threshold module configured to enable the ultraviolet exposure module after detecting a threshold of ultraviolet light, based on the sensed local ultraviolet conditions, has been reached.

15. The system according to claim 13, further comprising a display configured to display a level of current exposure to ultraviolet light and display a predicted future level of exposure to ultraviolet light.

16. The system according to claim 13, further comprising eyewear configured to be worn by the user, the eyewear including a frame coupled to the ultraviolet sensor.

17. The system according to claim 16, further comprising an audio interface coupled to the frame and coupled to the sensor local wireless transmitter, the audio interface including a microphone and a speaker.

18. A system comprising:
   eyewear configured to be worn by a user, the eyewear configured to reduce light reaching the user's eyes, the eyewear including:
      a frame;
      an ultraviolet sensor coupled to the frame, the ultraviolet sensor configured to sense local ultraviolet conditions; and
      a sensor local wireless transmitter coupled to the ultraviolet sensor; and
   a selective call receiver device including:
      a controller;

a device local wireless transceiver coupled to the controller and wirelessly coupled to the sensor local wireless transmitter;

a position determination module configured to determine a local position of the selective call receiver device;

a wireless wide area network transceiver coupled to the controller and wirelessly coupled to a wireless wide area network, the wireless wide area network transceiver configured to obtain local weather conditions by sending the local position of the selective call receiver device to a server and by receiving local weather conditions based on the local position of the selective call receiver device; and an ultraviolet exposure module configured to determine ultraviolet exposure based at least on the local weather conditions sensed by the ultraviolet sensor and the local weather conditions obtained by the network interface.

19. The system according to claim 18, further comprising an audio interface coupled to the frame and coupled to the sensor local wireless transmitter, the audio interface including a microphone and a speaker.

20. The system according to claim 1, wherein the local environmental conditions include forecast data for predicted future exposure.

* * * * *